US011263982B2

(12) United States Patent
Stuppi et al.

(10) Patent No.: US 11,263,982 B2
(45) Date of Patent: Mar. 1, 2022

(54) ADVANCED LEP DISPLAY MODE, ARCHITECTURES AND METHODOLOGIES FOR DISPLAY COMPENSATION (71) Applicant: Rockwell Collins, Inc., Cedar Rapids, IA (US)

(72) Inventors: Albert N. Stuppi, Springville, IA (US); Brian W. Walker, Cedar Rapids, IA (US); Alan M. Kuefler, Marion, IA (US); Duane A. Grave, Marion, IA (US)

(73) Assignee: Rockwell Collins, Inc., Cedar Rapids, IA (US)

( * ) Notice: Subject to any disclaimer, the term of this patent is extended or adjusted under 35 U.S.C. 154(b) by 0 days.

(21) Appl. No.: 17/112,603

(22) Filed: Dec. 4, 2020

(65) Prior Publication Data
US 2021/0174751 A1 Jun. 10, 2021

Related U.S. Application Data (60) Provisional application No. 62/945,674, filed on Dec. 9, 2019.

(51) Int. Cl.
G09G 3/34 (2006.01)
A61F 9/02 (2006.01)

(52) U.S. Cl.
CPC ............ G09G 3/3406 (2013.01); A61F 9/022 (2013.01); A61F 9/023 (2013.01); G09G 2320/0626 (2013.01); G09G 2330/021 (2013.01); G09G 2360/144 (2013.01)

(58) Field of Classification Search
None
See application file for complete search history.

(56) References Cited

U.S. PATENT DOCUMENTS

| 7,002,546 | B1* | 2/2006 | Stuppi | G09G 3/3413 345/102 |
| 7,022,546 | B2 | 4/2006 | Spooner et al. | |
| 7,202,852 | B2* | 4/2007 | Harvie | A61F 9/022 345/158 |
| 2003/0020677 | A1 | 1/2003 | Nakano | |
| 2003/0095705 | A1* | 5/2003 | Weast | G06T 11/001 382/167 |
| 2014/0002475 | A1* | 1/2014 | Oh | A61B 8/461 345/589 |

OTHER PUBLICATIONS

Extended Search Report for European Application No. 20212891.4 dated May 12, 2021, 13 pages.
Federal Aviation Administration OK-18-1812, AAM-400, "Laser Eye Protection (LEP) Perceptual Effects on Aviation", 2 pages, Downloaded Mar. 4, 2021.
LaserPointerSafety.com, A Comprehensive Resource for Safe and Responsible Laser Use, "Concerned about laser pointers? Want them used safely?", https://www.laserpointersafety.com, downloaded Mar. 4, 2021, 11 pages.

* cited by examiner

Primary Examiner — Dorothy Harris
(74) Attorney, Agent, or Firm — Suiter Swantz pc llo (57) ABSTRACT A display having a variably controlled backlight and/or driver is disclosed. The backlight includes a first light source that emits light within a first spectral power distribution and has a first radiant power output. A second light source emits light within a second spectral power distribution matched to an optical filter for producing a perceived chromaticity and luminosity matching the perceived display appearance without the optical filter.

12 Claims, 11 Drawing Sheets

ADVANCED LEP DISPLAY MODE, ARCHITECTURES AND METHODOLOGIES FOR DISPLAY COMPENSATION

CROSS REFERENCE TO RELATED APPLICATION

The present application claims priority under 35 U.S.C. 119 to U.S. Provisional Patent Application 62/945,674 filed on Dec. 9, 2019.

FIELD OF THE INVENTION

The invention relates to displays, and more particularly, to a laser eye protection optimized and compensated display.

BACKGROUND OF THE INVENTION

Laser pointer devices and the like are available in multiple colors (wavelengths) and have been increasingly utilized to frustrate and disable flight operations (see, e.g., Federal Aviation Administration OK-18-1812, AAM-400, *Laser Eye Protection (LEP) Perceptual Effects on Aviation*; and LaserPointerSafety.com. (Incorporated herein by reference in accordance with MPEP 608.01(p), 37 CFR 1.57(e)).

Various protective eyewear (goggles and the like) are available to absorb at least some wavelengths of laser light (see, e.g., Gentex Corporation, 324 Main ST, Carbondale, Pa. 18407; and PerriQuest Defense Research Enterprises, 639 Research Parkway, Meriden, Conn. 06450). However, such protective eyewear skews the perception of display colors on crew instrumentation. This increases crewmember workload and response time.

Color skewing caused by protective eyewear can be corrected at the display. Grayscale definitions can be changed at the display driver level. For displays with independent backlights the correction can also be made at backlight level, the display level. For independent backlights, Light-emitting diode (LED) arrays have shown great potential as a light source in liquid-crystal display (LCD) backlighting systems. When compared to other light sources such as incandescent or fluorescent light sources, LED arrays are desirable for their low-temperature performance, ease of heat-sinking, dimming range, small size, low power consumption, relatively low cost, luminous efficacy, and directional emission.

Color correction may be applied using the concept of modes. For example, current LCD displays are required to operate in day time (DAY mode), night time (NIGHT mode, and at night time when the pilot is wearing night vision goggles (NVG mode). In NIGHT mode luminance is limited. In NVG mode color correction is often applied. In this case, color is skewed by addition of a night vision filter to the display, rather than they eyewear worn by the pilot.

The idea of color correction by optical mode can be extended laser eye protection. In laser eye protection mode (LEP mode) the color of the display is skewed by the eyewear. The correction may be at the display level, the backlight level, or both. In the case of an LED with an independent LED backlight, the color may be corrected to meet display requirements by changing the color of the LED output. This may be accomplished by having different colors of LEDs and varying the luminance (drive current) of each type of LED, or using different sets of LEDs.

In LEP mode the color correction applied can changed depending upon which laser eye protective filter the pilot is wearing. The color correction can be applied in the LED backlight, by redefining grayscale luminance values in the display driver, or both. The system may be dynamic by automatically selecting the appropriate compensation depending upon the protective eyewear worn.

The same color correction principle applies to emissive displays such as organic light emitting diode displays (OLEDs). In this case, with no independent backlight, the correction must be applied by redefining grayscale driver luminance values.

Other display modes besides DAY, NIGHT, NVG, and LEP are possible. For example, a nuclear flash blindness (NFB) mode could be defined which drastically increases display luminance in response to a nuclear event.

It is another object of the invention to provide a display having consistent color uniformity regardless of whether a crewmember is viewing the display with or without an optical amplifier or filter.

It is yet another object to provide an optical feedback system that controls luminance and chromaticity of displays having light sources with different spectral outputs.

It is still another object of the invention to utilize pixel bias or pulse-width modulation techniques to isolate and measure differently-colored light sources in a backlight.

It is still another object of the invention that it is applicable to any display system that is based on the human visual response. independent of radiation sources or methods of producing a spatially modulated image.

SUMMARY OF THE INVENTION

Multiple spectral sources have been utilized in display backlights (e.g., U.S. Pat. No. 7,002,546 incorporated herein by reference). In some implementations, different colors (wavelengths) are added to white in order to meet optical requirement and luminance values. In operation, the present disclosure describes an apparatus and method for adjusting the intensity of a first light source relative to the intensity of a second light source in response to a perceived display color space change caused by, e.g., a crewmember donning laser eye protection altering perceived display chromaticity and luminance relative to a desired chromaticity and luminance.

The invention further provides an optical feedback and control system for an LCD backlight having a first light source and a second light source, each of the light sources emitting light having a different spectral power distribution. A Laser Eye Protection (LEP) matched color space selector either detects or allows a user to select a radiant power of light emitted by the first and second light sources. In some embodiments a processor is connected to the LEP matched color space selector and calculates chromaticity and luminance values of the emitted light based on the detected radiant power and the spectral power distribution of each of the first and second light sources. The processor compares the calculated chromaticity and luminance values with desired chromaticity and luminance values, respectively. A controller is operationally connected to the processor. The controller adjusts one or more of the radiant power of the first light source and the radiant power of the second light source in response to a difference between the calculated chromaticity and luminance values and the desired chromaticity and luminance values.

DETAILED DESCRIPTION OF THE DRAWINGS

Figure 1:
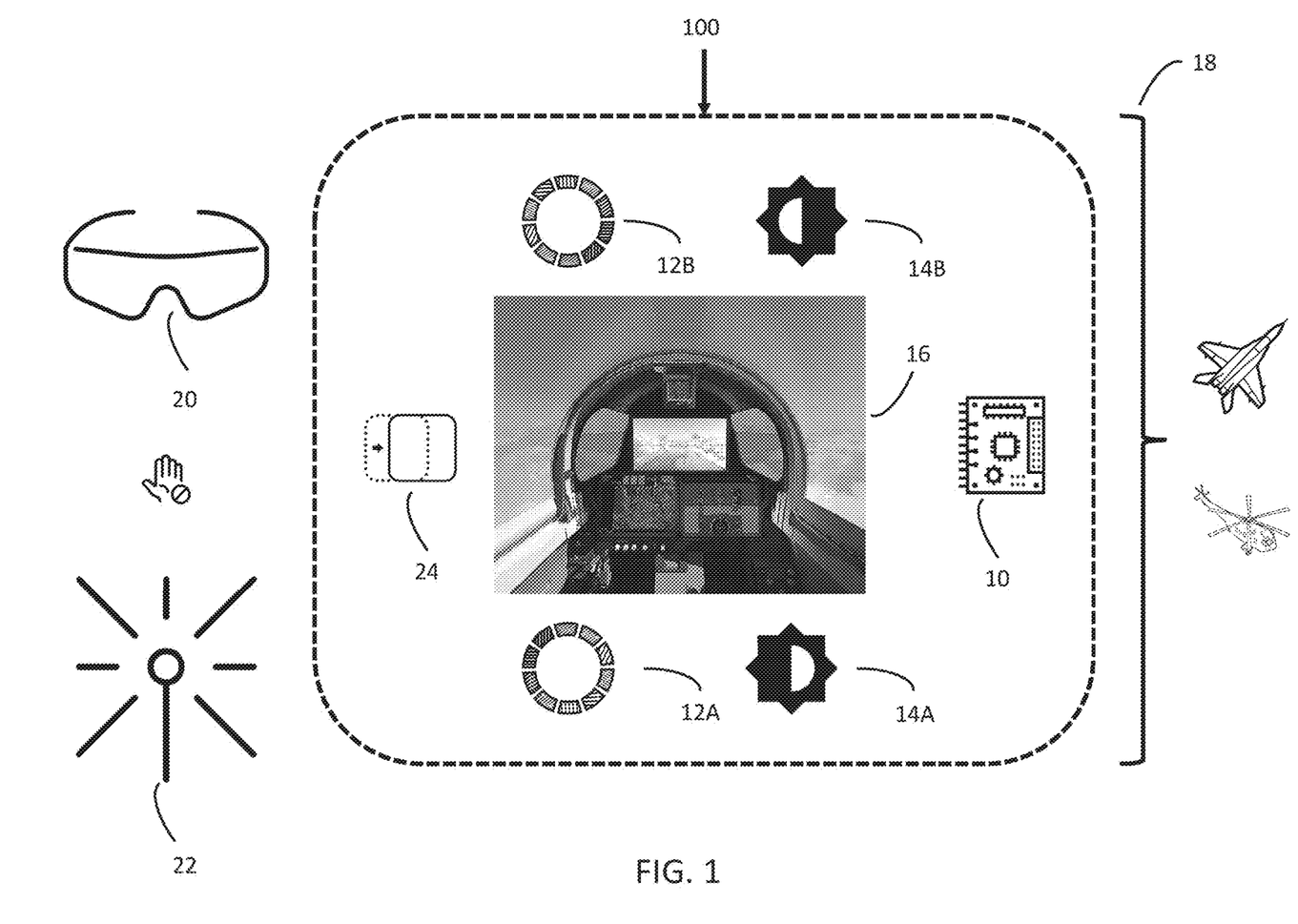
FIG. 1 is an environmental illustration of an embodiment of the present invention for use in an aircraft cockpit.
Figure 2:
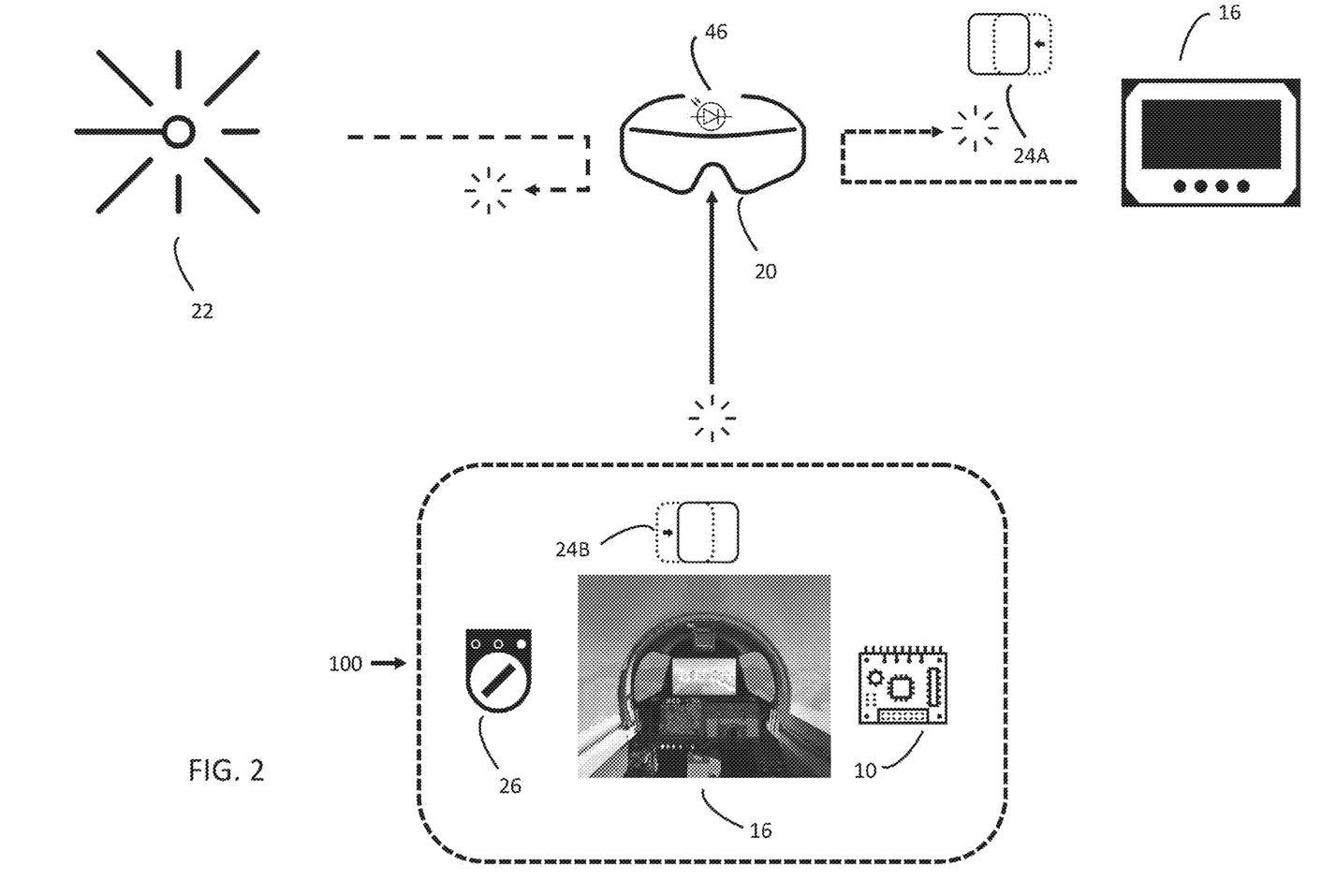
FIG. 2 is an environmental illustration of an embodiment of the present invention for use in an aircraft cockpit.

Turning now to the Figures, in which similar reference numbers refer to similar components, a display system according to a preferred embodiment of the invention is shown. FIG. 1 is an environmental illustration of an embodiment of the present invention 100 may include a controller 10 for driving a first chromaticity 12A to a second chromaticity 12B and in some embodiments a first luminance 14A to a second luminance 14B. for use in an aircraft 18 cockpit having one or more displays 16 in one or more instrument panels. In operation a pilot or crewmember may be required to shield their vision with a Laser Eye Protection goggles 20 or the like to shield their eyes from LASER 22 apparatus. The invention 100 controller 10 may shift the display from a first color space 24A to a second color space 24B by differentially illuminating the display(s) so as to compensate for the perception effects associated with the LEP 20 goggles or the like. A pilot or crewmember may utilize a color space selector 16 (LEP selector) to drive the controller 10 backlight system 28 to selectively change the color space optimally for the selected LEP via the processor 44 and circuit board 30. Likewise, as illustrated in FIG. 2, the invention 100 via controller 10 may automatically be paired with protective eyewear (such as LEP 20 or the like) wherein the protective eyewear includes a detector 46 for detecting the chromaticity 12 and luminance 14 between a user's eye and the protective eyewear 16 such that the controller 10 may drive the backlight system 28 (or micro-LEDs) to a compensated output appropriate to the displayed content and optimized for flight operations. The goggles 16 may be wirelessly 50 connected to the system 100 via Bluetooth, UWB, WiFi, LiFi, or the like.

Figure 3A:
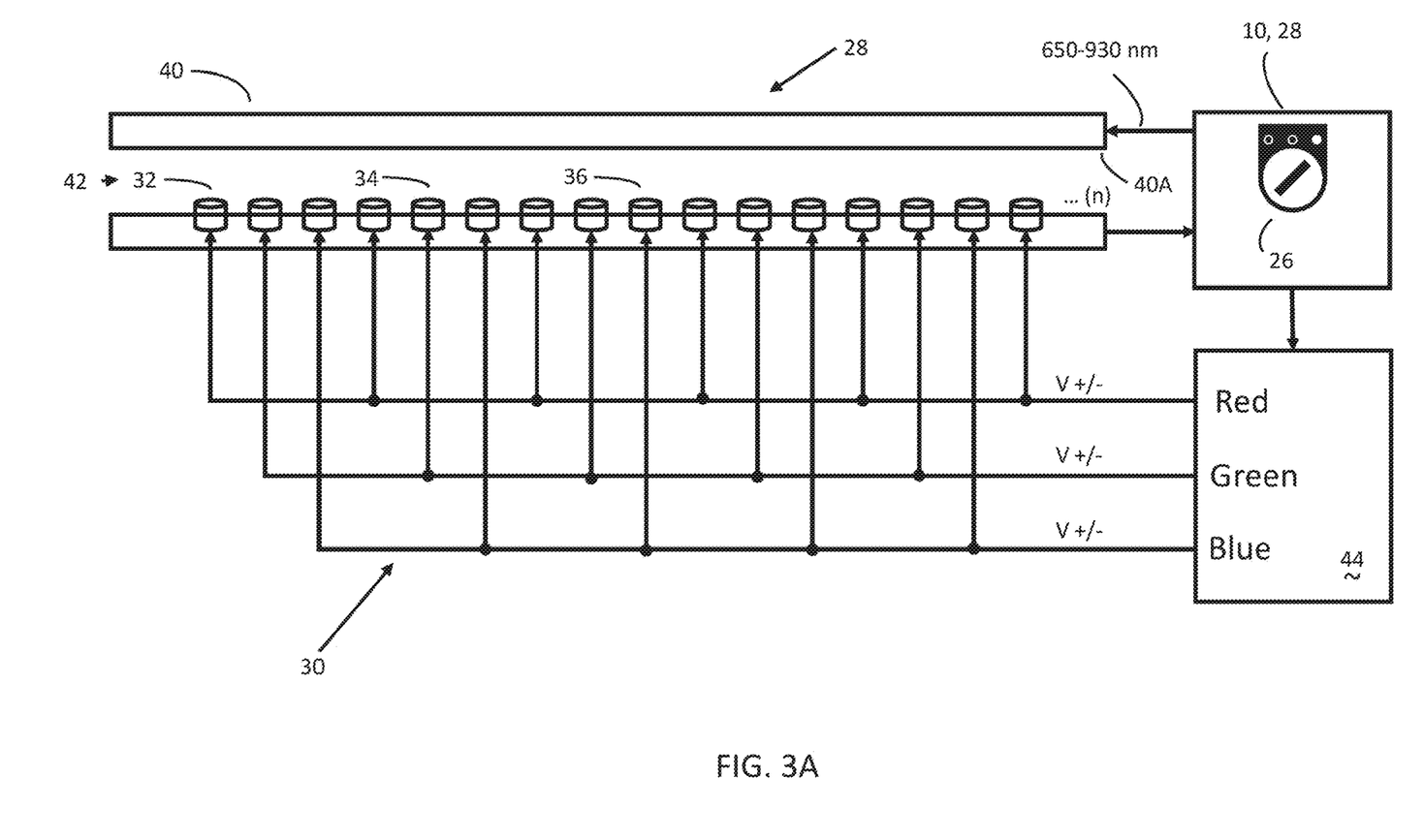
FIG. 3A is a diagram of a user selectable display compensation system of an LED-based LCD backlight according to an embodiment of the invention.
Figure 3B:
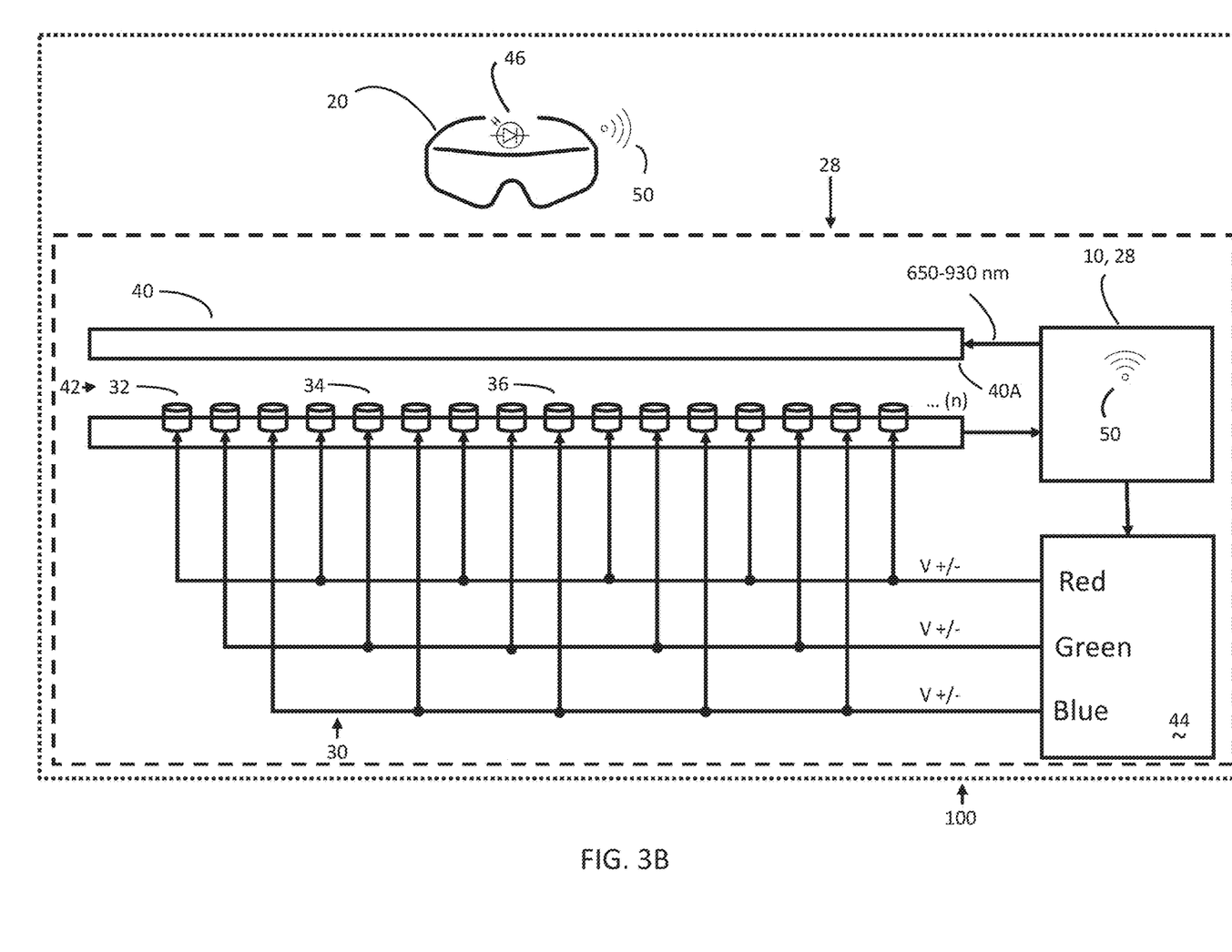
FIG. 3B is a diagram of an automatic display compensation system of an LED-based LCD backlight according to an embodiment of the invention.
Figure 4A:
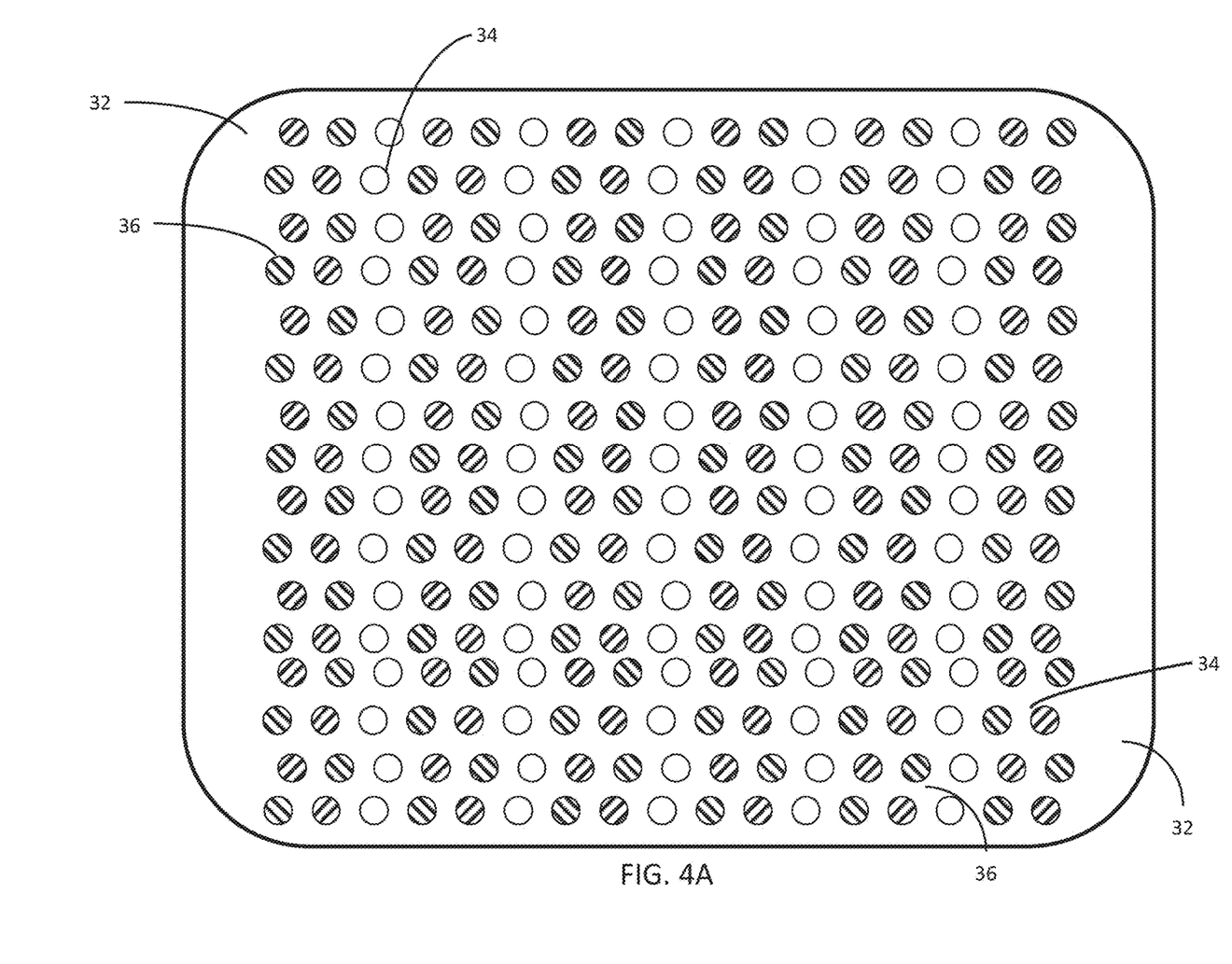
FIG. 4A and FIG. 4B are a vertical plan view of the LCD backlight shown in FIG. 1.

Turning now to FIGS. 3 and 4 wherein the present disclosure is indicated generally by reference number 10. The invention 100 (FIG. 1) includes a backlight system 28 with a printed wiring board 30 upon which a plurality of light-emitting diodes (LEDs) are mounted. In this embodiment, the LED's include a red LED array 32 comprising a plurality of red LEDs, a green LED array comprising a plurality of green LEDs 34, and a blue LED array 36 comprising a plurality of blue LEDs. The precise number, color, and placement of the red, green and blue LED arrays depend on the luminance and chromaticity that is desired from the backlight. In FIGS. 3 and 4, the red, green and blue LED arrays comprise equal numbers of LEDs (FIG. 4), and the differently colored LEDs are evenly distributed upon the printed wiring board (FIGS. 3A & 3B).

LED arrays 32, 34, 36 are connected to a controller 10 (with backlight system 28) by electrical circuitry 30. Controller 10 provides a variable electrical current to each of the LEDs to vary the radiant power output of the LEDs. Controller 10 is also capable of controlling the radiant power output of the LEDs through pulse width modulation techniques (and/or by individual pixel bias), in which current to the LEDs is adjusted in order to optimize display output under different circumstances (e.g., pilot or crewmember donning LEP or night vision goggles).

In some embodiments, an optical mixing device such as a diffuser 40 is placed between LEDs 32, 34, 36 and the LCD stack (not shown). Diffuser 40 is substantially planar and is preferably made of translucent plastic or other suitable material. Light from the LEDs is intermixed in the free space 42 between board 30 and diffuser 40, and is further mixed within the diffuser to provide a homogeneous light source for the LCD. A LEP matched color space selector 26 (in some embodiments, along with, e.g., a photodiode (not shown), on a printed wiring board 30 and detects the intensity of the portion of the LED light that has reflected off of a diffuser surface 40A.

Using pulse-width modulation techniques, light from each of the red, green and blue LED arrays may be individually selected by LEP matched color space selector 26. The light emitted by each of the LED arrays is isolated from the other LED arrays by staggering the "off" signals sent to each of the LED groups during a pulse-width modulation cycle. In a currently preferred implementation, red LED array 32 is turned off first at time t1. Green LED array 34 is next turned off at time t2, and blue LED array 36 is turned off at time t3. At time t4, the red LED array is again activated; at time t5, the green LED array is activated; and at time t6 the blue LED array is activated. In some embodiments, the intensity of light from blue LED array 34 may be detected (via a photodiode or the like, not shown) between time t2 and time t3 because during that time only the blue LED array is activated. The intensity of light from red LED array 32 may be detected between time t4 and time t5 because during that time only the red LED array is activated. The intensity of light from green LED array 34 may be detected by rearranging the order in which the LED arrays are switched on and off in a subsequent cycle. In this fashion, a LEP matched color space selector 26 can be utilized to selectively adjust the intensity of light from each of the red, green, and blue LED arrays for a particular operation (e.g., goggle type). It should be mentioned that for a typical pulse width frequency of 100 Hertz, the elapsed time between time t1 and time t2 (and between times t2 and t3, etc.) is preferably measured in milliseconds.

LEP matched color space selector 26 is connected to a processor 44. The processor calculates a resulting mixed chromaticity and luminance contributions for each of red, green, and blue LED arrays 32, 34, 36 based on the selection (or detected operating environment) made on the LEP matched color space selector 26. Where a detector 46 (FIG. 2) or the like is utilized to determine crewmember configuration (i.e., type of filter or amplification worn), in some embodiments, a detector may also measure intensities, or radiant power outputs, of the LED arrays between a crewmember's eyes and any goggles or filters or the like so as to directly measure chromaticity and luminance. Prior to deploying and operating the backlight, the intensities of the LED arrays may be measured (in some embodiments) at the desired chromaticity and luminance levels. Then, during operation, processor 44 determines the chromaticity and luminance of each LED array based on the detected intensity of the light from each array. Processor 44 compares the combined luminance of the red, green and blue LED arrays, which comprises the total luminance of the LCD backlight, with a desired or predetermined total backlight luminance. The processor also compares the calculated chromaticity values for each of the red, green, and blue LED arrays with desired or predetermined chromaticity values. If there is a difference between the calculated values and the desired values of luminance and/or chromaticity, the processor sends commands to controller 20 to adjust the output of one or more of the LED arrays. This is accomplished either by adjusting the peak current to an LED array, or by adjusting the pulse length of the current to the LED array. The chromaticity of the output light is reasonably controlled by maintaining a defined luminance ratio between red, green, and blue LED arrays.

FIG. 3B depicts another embodiment of the invention that may be used in applications where any filter or apparatus utilized by a crewmember to interpret a display include a detector 46 (and e.g., a wired or wireless connector to the display controller 10) to automatically adjust the display output to compensate the display to output the desired color space.

Figure 3C:
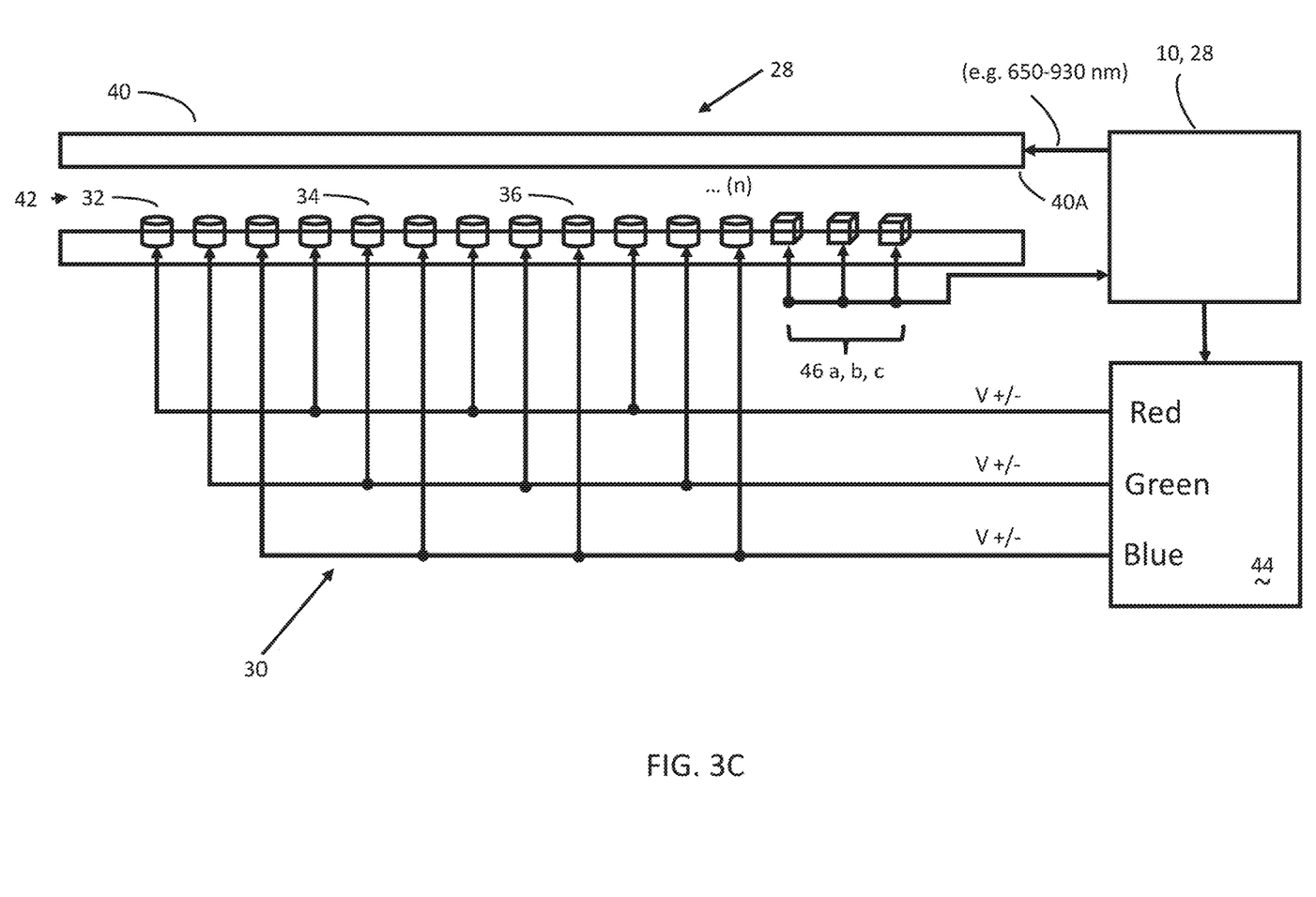
FIG. 3C is a diagram of an automatic display compensation system of an LED-based LCD backlight according to an embodiment of the invention.

In other embodiments (FIG. 3C) pulse-width modulation techniques may not be available or where such techniques are undesirable. The LCD backlight system 28 according to this embodiment includes first, second, and third LEP matched color space selector 26s 46 *a*, 46 *b*, 46 *c*. First LEP matched color space detector 46*a* detects light according to the standard x chromaticity function. Second LEP matched color space detector 46*b* detects light according to the standard y chromaticity function. Third LEP matched color detector 46 *c* detects light according to the standard z chromaticity function. Color matching filters 48*a*, 48*b*, and 48*c* are placed between waveguide 38 and LEP matched color space selector 46*a*, 46*b*, and 46*c* as shown. Tri-stimulus values X, Y, and Z are derived from the detected x, y, and z chromaticity functions, and chromaticity values u' and v' are then calculated according to known algorithms. As previously stated, the luminance value of the detected light is proportional to the Y tri-stimulus value. Differences between calculated and desired chromaticity and/or luminance may be corrected by varying the current sent to one or more of red, green, and blue LED arrays 32, 34, 36. By balancing the current sent to the LED arrays in this manner, the output of LCD backlight 28 *a* may be optimized for a particular crewmember LEP 20.

Figure 4B:
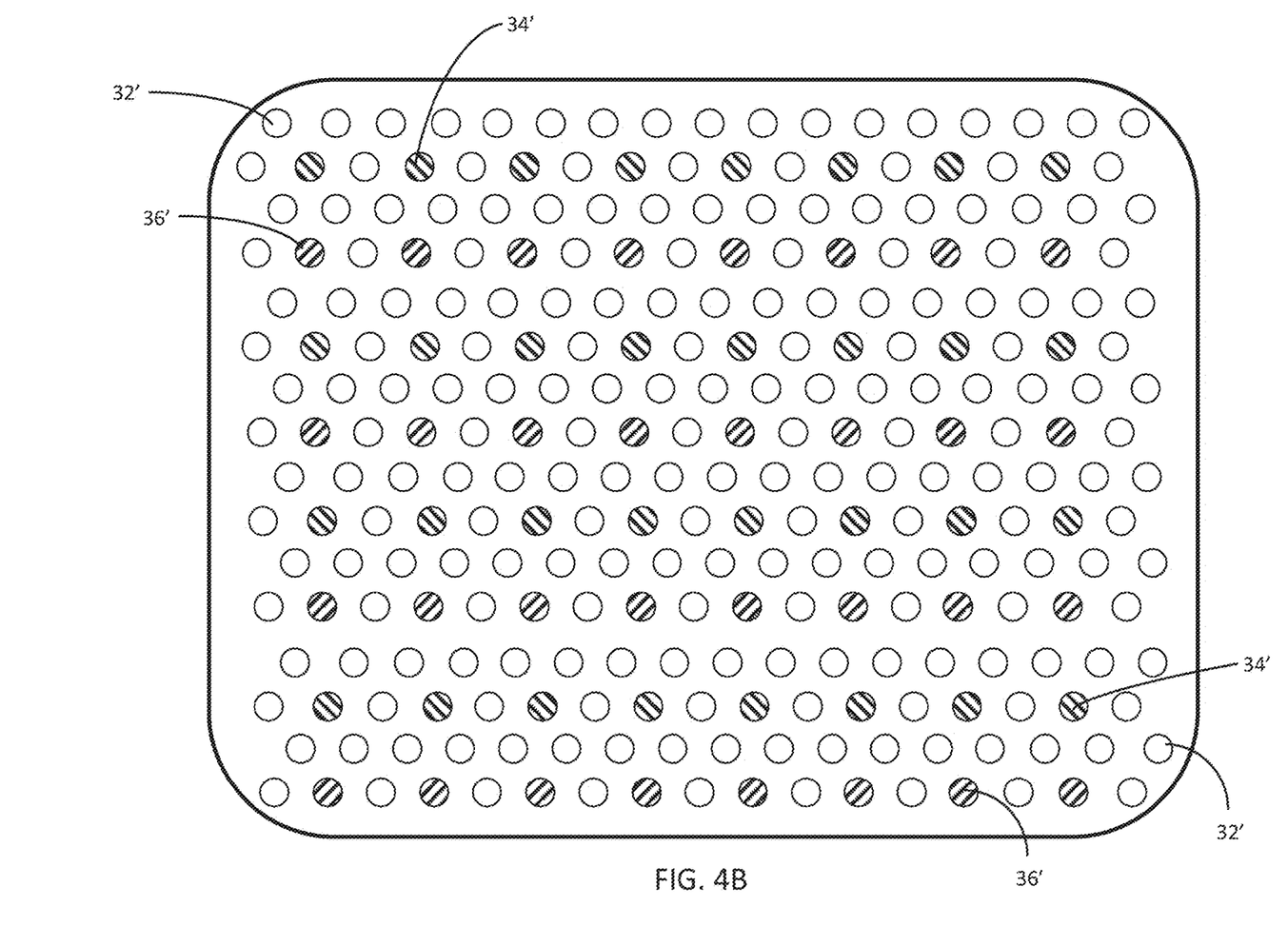
Figure 5A:
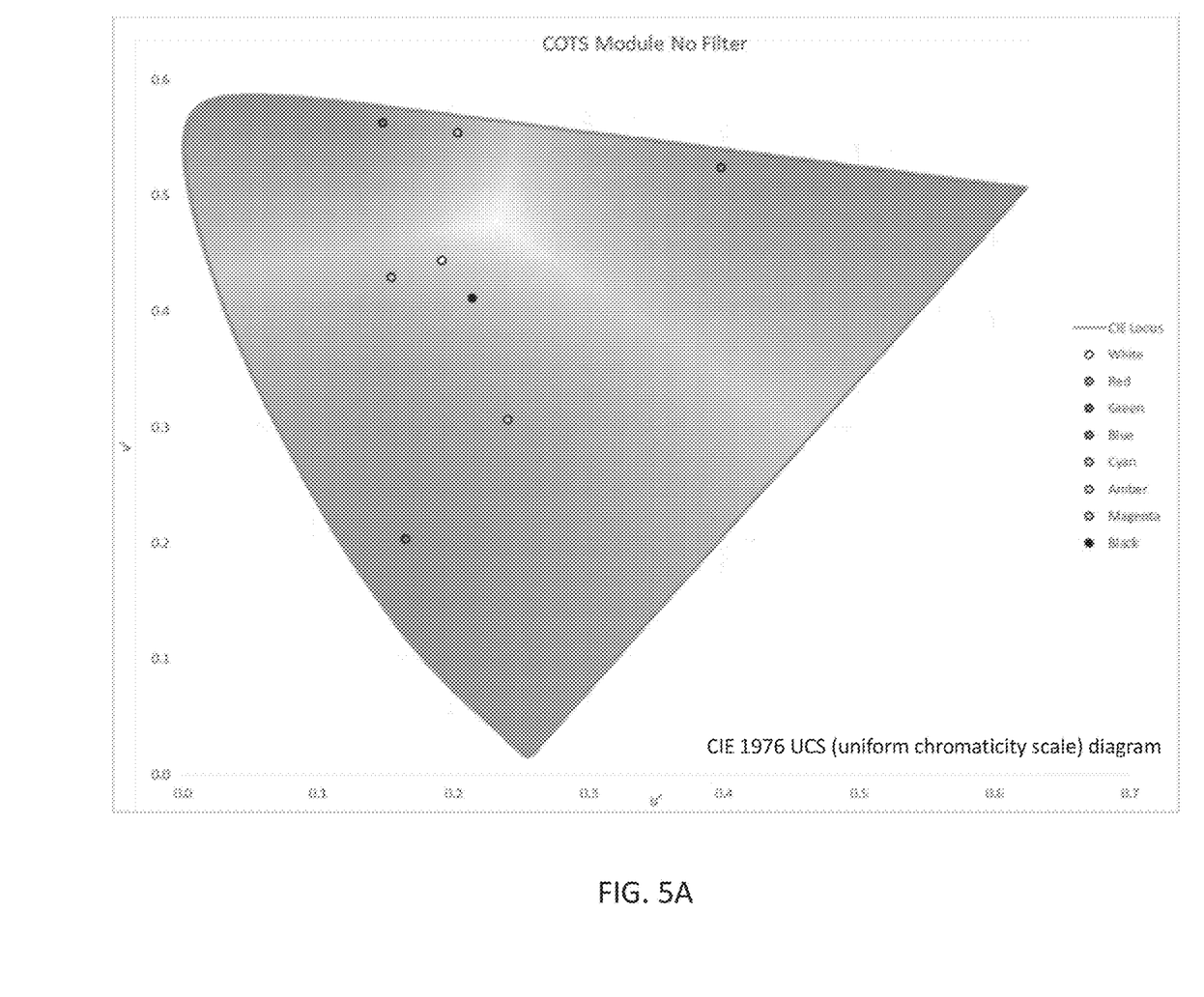
FIG. 5A is a CIE 1976 USC diagram of a preferred display output viewed without an LEP or amplifier.
Figure 5B:
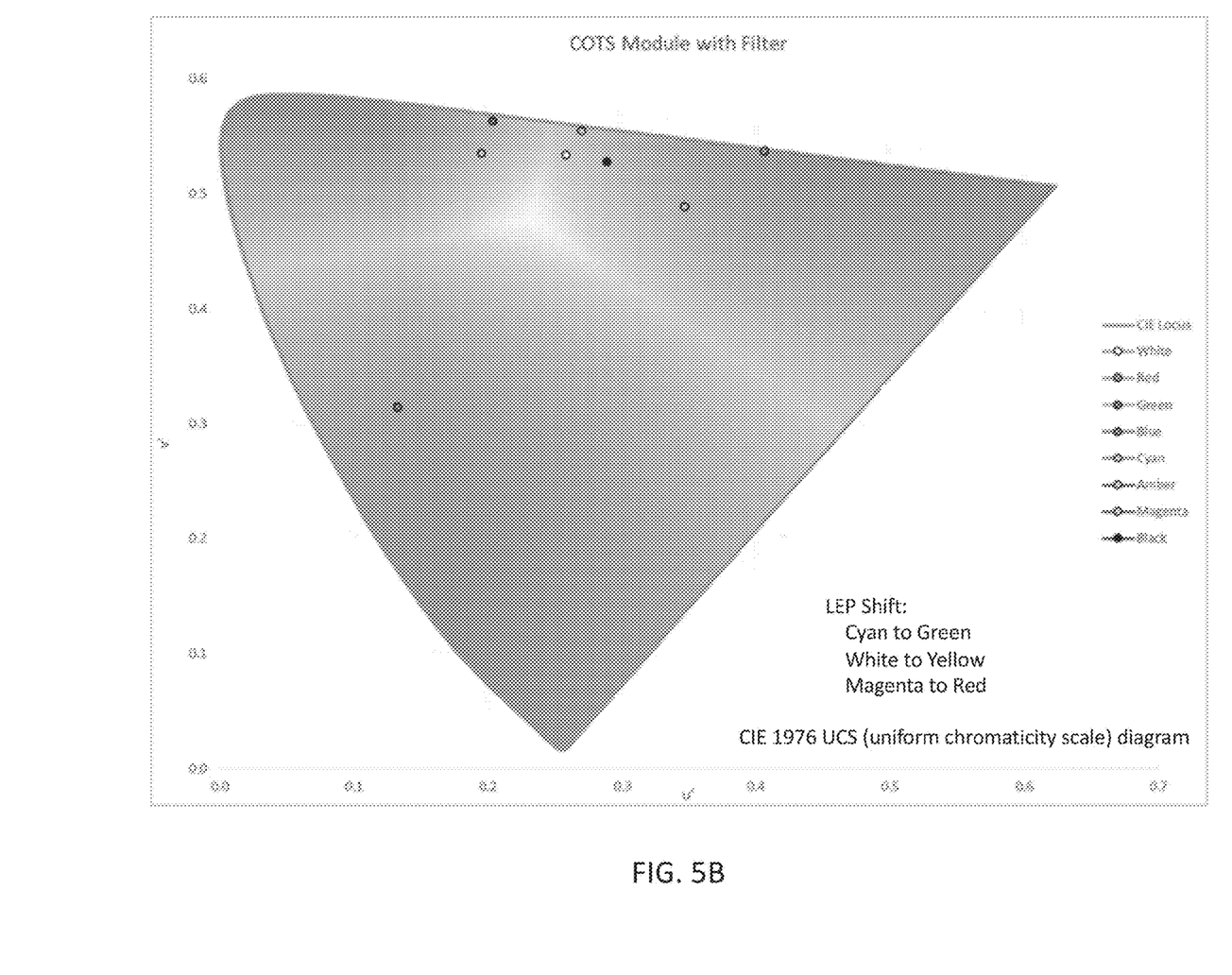
FIG. 5B is a CIE 1976 USC diagram of a preferred display output viewed with an LEP or amplifier.
Figure 6A:
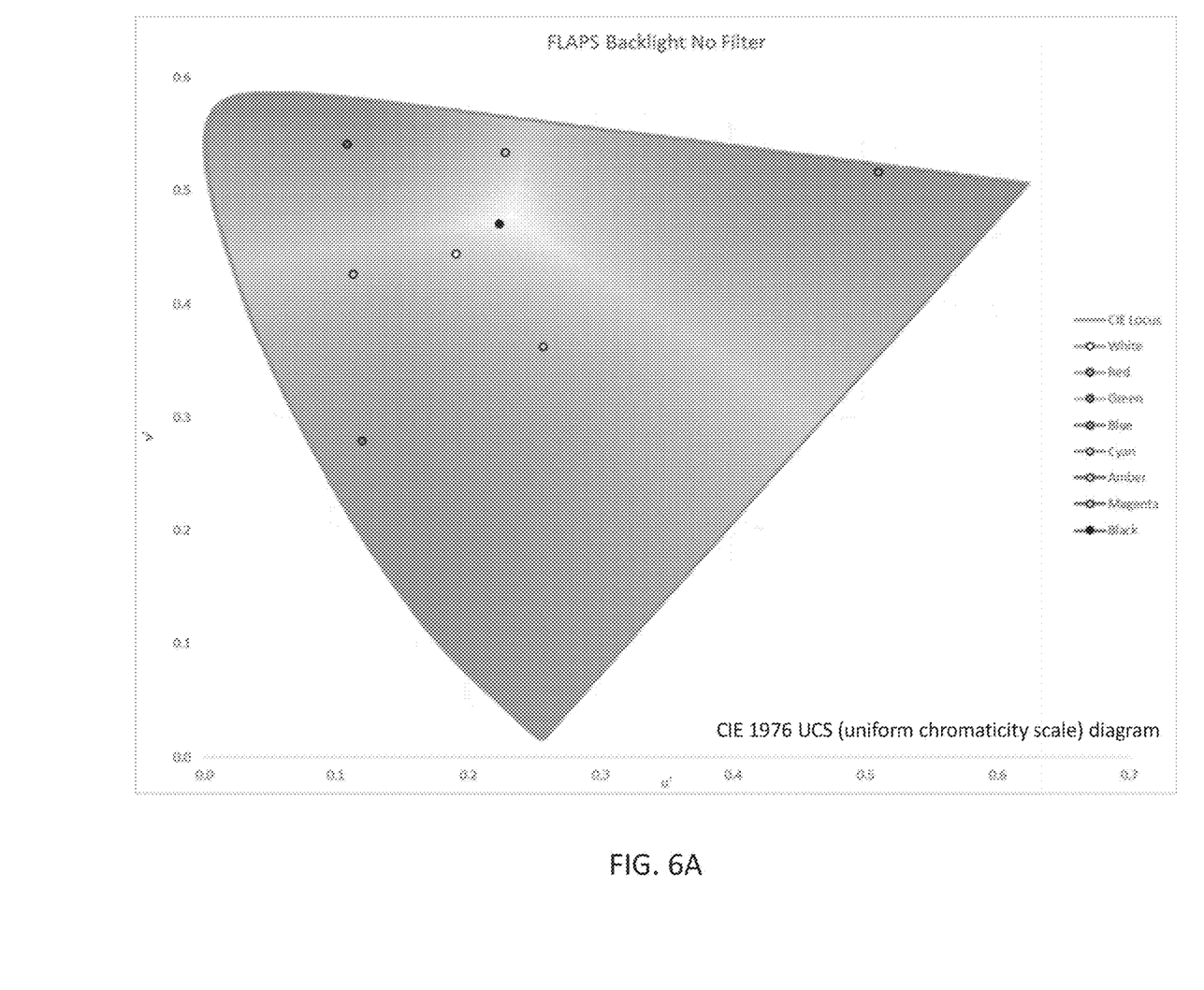
FIG. 6A is a CIE 1976 USC diagram of a preferred display output of an embodiment of the present invention viewed without an LEP or amplifier.
Figure 6B:
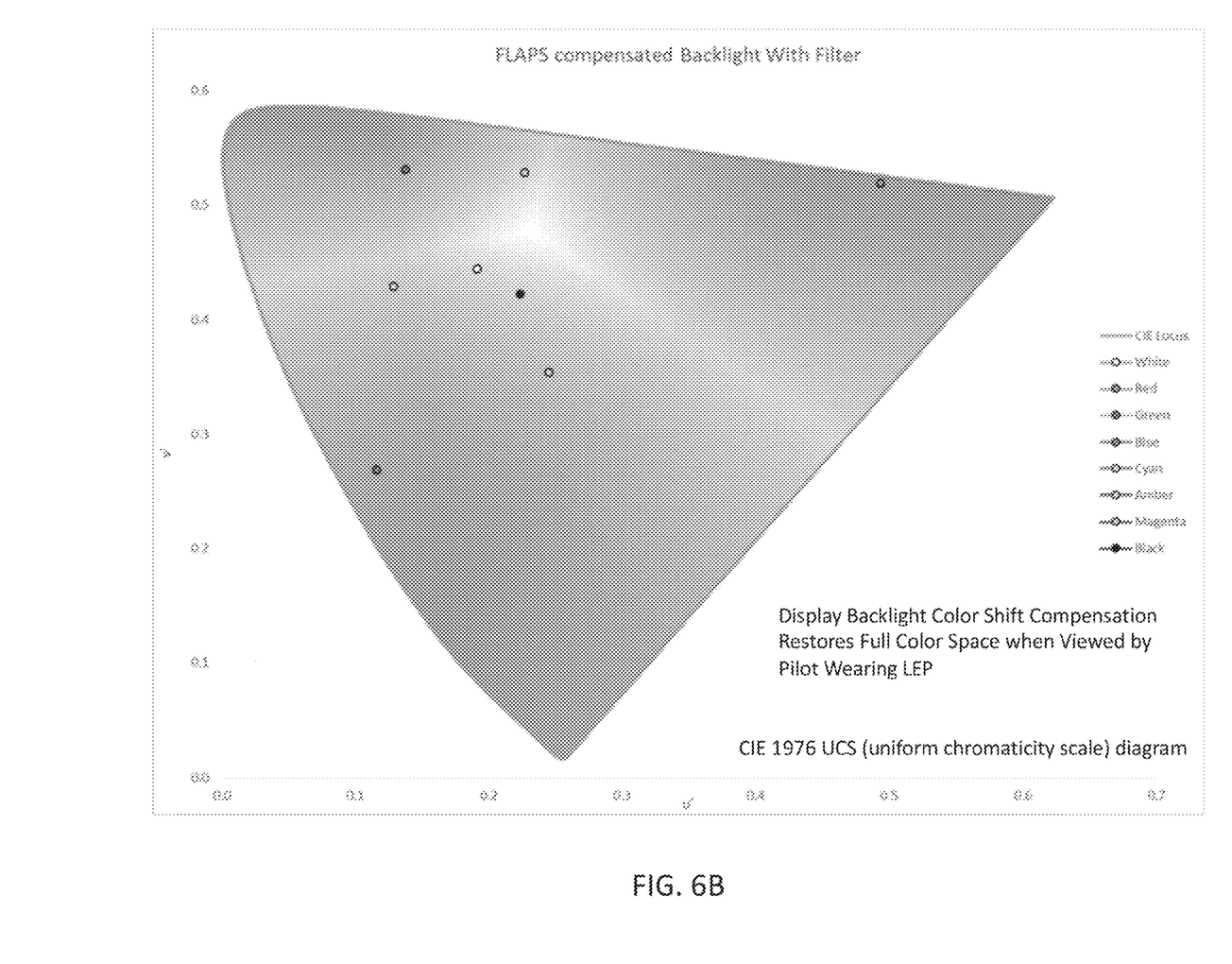
FIG. 6B is a CIE 1976 USC diagram of a preferred display output of an embodiment of the present invention viewed with an LEP or amplifier.

The invention may be used to effect real time chromaticity control of an LCD backlight. Changing the backlight chromaticity depending on the type of information displayed may make the display more readable. For example, if the information being displayed on an avionics display changes from video to weather radar, the chromaticity of the backlight may also be changed to produce a chromaticity optimized for the new information being displayed optimized and compensated for a crewmember worn devices. As another example, an LCD backlight used in an avionics display may be required to adjust luminance levels to 0.05 fL or less during night flying. At such levels it can be difficult to see red display text and symbology. Red luminance may be increased to adapt to the new conditions. Such an LCD display is shown in FIG. 4B, in which a plurality of white LEDs 32' and a plurality of red LEDs 34' are mounted on a printed wiring board 30. As with previous embodiments, the differently colored LEDs are intermixed on the printed wiring board. In some embodiments other colored LEDs 36' may also be intermixed. When it is desired to change the red luminance, the current flowing to red LEDs 34' is changed relative to the current flowing to white LEDs. FIGS. 5A, 5B, 6A, and 6B are chromaticity diagrams upon which is plotted exemplary effects of current changes relevant to a display driven to accommodate crewmember worn goggles 20.

The invention may be varied while keeping with the spirit of the invention as herein described. For example, the exact number and color of the LEDs may be selected according to backlight requirements. The light-mixing methodology may include one or more of a bulk diffuser, holographic diffusers, waveguide, free-space propagation, or the like. If a waveguide is used, part or all of the LEDs may be disposed along an edge of the waveguide to create what is generally known as an edge-lit waveguide. The LEP matched color space selector 26 may be placed anywhere that is convenient, as long as the LEP matched color space selector 26 can be confidently and dependably reached by pilots and crew members. In some embodiments the laser eye protection 20 may communicate with the required selector 26 wirelessly or otherwise.

The invention as disclosed herein provides a method of monitoring and controlling, in real time, both the chromaticity and luminance of an LCD backlight. An advantage of the invention is that expensive sensing systems are not required to provide such real-time control.

Another advantage is that, in at least one embodiment, a LEP matched color space selector 26 may be used to select compensated color space dependent on a pilot or crewmember worn laser eye protection device 20. The selector 26 selects luminance for driving differently-colored light sources. Staggered pulse-width modulation techniques may be utilized to isolate each of the colors such that the LEP matched color space selector 26 can accurately provide the optimum output to each light source.

Another advantage is that ambient light, such as sunlight, may also be measured and mitigated using the disclosed techniques of the invention. This feature substantially eliminates display "washout" that is typically (but not exclusively) encountered when sunlight directly contacts an LCD display screen.

Still another advantage is that the invention may be used with LCD backlights employing red, green, and blue LED arrays as well as other color schemes, such as white and red LED arrays.

Yet another advantage is that the invention may be used with LED-based LCD backlights using pulse-width modulation controls as well as LCD backlights using current modification techniques to vary backlight luminance.

Yet another advantage is that the invention may be used with LCD backlights that use other types of illumination, such as fluorescent lighting.

In other embodiments the compensation of the present invention may be utilized to improve display readability for persons with certain color blindness conditions.

While the invention has been disclosed in its preferred form, the specific embodiments thereof as disclosed and illustrated herein are not to be considered in a limiting sense as numerous variations are possible. The subject matter of the invention includes all novel and non-obvious combinations and subcombinations of the various elements, features, functions and/or properties disclosed herein. No single feature, function, element or property of the disclosed embodiments is essential to all of the disclosed inventions. Similarly, where the claims recite "a" or "a first" element or the equivalent thereof, such claims should be understood to include incorporation of one or more such elements, neither requiring nor excluding two or more such elements.

It is believed that the following claims particularly point out certain combinations and subcombinations that are directed to the disclosed inventions and are novel and non-obvious. Inventions embodied in other combinations and subcombinations of features, functions, elements and/or properties may be claimed through amendment of the present claims or presentation of new claims in this or a related application. Such amended or new claims, whether they are directed to a different invention or directed to the same invention, whether different, broader, narrower or equal in scope to the original claims, are also regarded as included within the subject matter of the invention of the present disclosure.

The invention claimed is:

1. A variably controlled aircraft display, comprising:
    laser eye protection goggles including an optical filter for protecting crewmember vision, the laser eye protection goggles including a detector configured to detect a radiant power and a spectral power distribution of light between the optical filter and an eye of the crewmember;
    a first light source of a liquid crystal display backlight emitting light within a first spectral power distribution and having a first radiant power output, wherein the first light source is a first array of light-emitting diodes;
    a second light source of the liquid crystal display backlight emitting light within a second spectral power distribution and having a second radiant power output, wherein the second light source is a second array of light-emitting diodes;
    a processor wirelessly connected to the laser eye protection goggles, for driving chromaticity and luminance values of the emitted light based on the first and second radiant power outputs, the processor configured to determine calculated chromaticity and luminance values based on the radiant power and spectral power distribution detected by the detector; and
    a controller, operationally connected to the processor, that is configured to adjust one or more of the first radiant power output and the second radiant power output in response to a difference between the calculated chromaticity and luminance values and desired chromaticity and luminance values to compensate for a perception effect associated with the optical filter of the laser eye protection goggles.

2. The display of claim 1, wherein the first array of light-emitting diodes emits red light, the second array of light-emitting diodes emits green light, and further including a third array of light-emitting diodes that emits blue light at a third radiant power output; wherein the detector is configured to detect the radiant power outputs of the first, second, and third arrays of light-emitting diodes.

3. The display of claim 1, wherein the first and second arrays of light-emitting diodes are selectively activated by the controller such that for a first predetermined time, the first array is activated and the second array is not activated; for a second predetermined time, the second array is activated and the first array is not activated; and for a third predetermined time, the first array and the second array are activated.

4. The display of claim 3, wherein the detector is configured to detect the first radiant power output during the first predetermined time, and wherein the detector is configured to detect the second radiant power output during the second predetermined time.

5. The display of claim 3, wherein for a fourth predetermined time, neither the first array nor the second array are activated.

6. The display of claim 5, wherein an ambient luminance is measured during the fourth predetermined time, and wherein the measured ambient luminance is subtracted from the luminance of light detected during at least one of the first and second predetermined times.

7. The display of claim 1, wherein the first and second arrays of light-emitting diodes are selectively activated by the controller such that for a first predetermined time, the first array is not activated and the second array is activated; for a second predetermined time, the second array is not activated and the first array is activated; and for a third predetermined time, the first array and the second array are activated.

8. The display of claim 3, wherein the detector is configured to detect the second radiant power output during the second predetermined time, and wherein the detector is configured to detect the first radiant power output during the first predetermined time.

9. The display of claim 3, wherein for a fourth predetermined time, both the first array and the second array are activated.

10. The display of claim 1, wherein the detector is further configured to detect and report a first predetermined tri-stimulus value of light emitted by the first and second light sources, the laser eye protection goggles further comprising:
    a second detector configured to detect a second predetermined tri-stimulus value of light emitted by the first and second light sources; and
    a third detector configured to detect a third predetermined tri-stimulus value of light emitted by the first and second light sources, wherein the processor is further connected to a color space selector and the third detector is configured to calculate chromaticity and luminance values of emitted light based on the first, second, and third predetermined tri-stimulus values detected by the first, second, and third detector.

11. The display of claim 1, wherein the controller is configured to control current to the first and second light sources using pulse-width modulation, and further wherein the first and second radiant power outputs are selectively adjusted by altering a pulse-width modulation pattern to the first and second light sources.

12. The display of claim 1, wherein the controller is configured to control current to the first and second light sources using pulse-width modulation, to improve display readability for persons with color blindness.

* * * * *